(12) United States Patent
Trees et al.

(10) Patent No.: US 9,254,171 B2
(45) Date of Patent: Feb. 9, 2016

(54) ELECTROSURGICAL INSTRUMENT WITH MULTI-STAGE ACTUATOR

(71) Applicant: Ethicon Endo-Surgery, Inc., Cincinnati, OH (US)

(72) Inventors: Gregory A. Trees, Loveland, OH (US); Randolph C. Stewart, Cincinnati, OH (US); Alex W. Kiturkes, Cincinnati, OH (US); William A. Crawford, Batavia, OH (US); Patrick J. Minnelli, Harrison, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 68 days.

(21) Appl. No.: 13/826,036

(22) Filed: Mar. 14, 2013

(65) Prior Publication Data

US 2014/0276777 A1 Sep. 18, 2014

(51) Int. Cl.
*A61B 18/18* (2006.01)
*A61B 17/56* (2006.01)
*A61B 18/14* (2006.01)
*A61B 18/00* (2006.01)

(52) U.S. Cl.
CPC ............. *A61B 18/18* (2013.01); *A61B 18/1445* (2013.01); *A61B 18/1447* (2013.01); *A61B 2018/00005* (2013.01); *A61B 2018/0063* (2013.01); *A61B 2018/00607* (2013.01); *A61B 2018/00916* (2013.01); *A61B 2018/00922* (2013.01); *A61B 2018/1455* (2013.01)

(58) Field of Classification Search
USPC .................................................... 606/41, 51
See application file for complete search history.

(56) References Cited

U.S. PATENT DOCUMENTS

| | | | |
|---|---|---|---|
| 4,805,823 | A | 2/1989 | Rothfuss |
| 5,415,334 | A | 5/1995 | Williamson, IV et al. |
| 5,465,895 | A | 11/1995 | Knodel et al. |
| 5,597,107 | A | 1/1997 | Knodel et al. |
| 5,632,432 | A | 5/1997 | Schulze et al. |
| 5,673,840 | A | 10/1997 | Schulze et al. |
| 5,704,534 | A | 1/1998 | Huitema et al. |
| 5,814,055 | A | 9/1998 | Knodel et al. |
| 6,500,176 | B1 | 12/2002 | Truckai et al. |
| 6,506,208 | B2 | 1/2003 | Hunt et al. |
| 6,783,524 | B2 | 8/2004 | Anderson et al. |
| 6,978,921 | B2 | 12/2005 | Shelton, IV et al. |
| 7,000,818 | B2 | 2/2006 | Shelton, IV et al. |

(Continued)

OTHER PUBLICATIONS

U.S. Appl. No. 61/410,603, filed Nov. 5, 2010.

(Continued)

*Primary Examiner* — Nicole F Lavert
(74) *Attorney, Agent, or Firm* — Frost Brown Todd LLC

(57) ABSTRACT

An apparatus comprises an end effector, a shaft, and a handpiece. The end effector is operable to manipulate tissue. The shaft is in communication with the end effector. The shaft includes a firing beam operable to actuate a portion of the end effector. The handpiece comprises a pivoting trigger that is operable to distally advance a firing beam driver to advance the firing beam. The handpiece also comprises an activation button and lockout assembly. The lockout assembly is movable between a locked and unlocked state. In the locked state, the lockout assembly blocks a portion of the firing beam driver from advancing. In the unlocked state, the lockout assembly allows the firing beam driver to advance. The activation button switches is operable to unlock the lockout assembly.

20 Claims, 15 Drawing Sheets

(56) References Cited

U.S. PATENT DOCUMENTS

| | | |
|---|---|---|
| 7,112,201 B2 | 9/2006 | Truckai et al. |
| 7,125,409 B2 | 10/2006 | Truckai et al. |
| 7,143,923 B2 | 12/2006 | Shelton, IV et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,303,108 B2 | 12/2007 | Shelton, IV et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,434,715 B2 | 10/2008 | Shelton, IV et al. |
| 7,721,930 B2 | 5/2010 | McKenna et al. |
| 8,408,439 B2 | 4/2013 | Huang et al. |
| 8,453,914 B2 | 6/2013 | Laurent et al. |
| 8,461,744 B2 | 6/2013 | Wiener et al. |
| 8,795,327 B2 | 8/2014 | Dietz et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 * | 4/2011 | Boudreaux et al. ............ 606/41 |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0116379 A1 | 5/2012 | Yates et al. |
| 2013/0023868 A1 | 1/2013 | Worrell et al. |
| 2013/0030428 A1 | 1/2013 | Worrell et al. |
| 2013/0123782 A1 | 5/2013 | Trees et al. |

OTHER PUBLICATIONS

U.S. Appl. No. 61/550,768, filed Oct. 24, 2011.

International Search Report dated May 20, 2014 for Application No. PCT/US2014/017106.

International Written Opinion dated May 20, 2014 for Application No. PCT/US2014/017106.

* cited by examiner

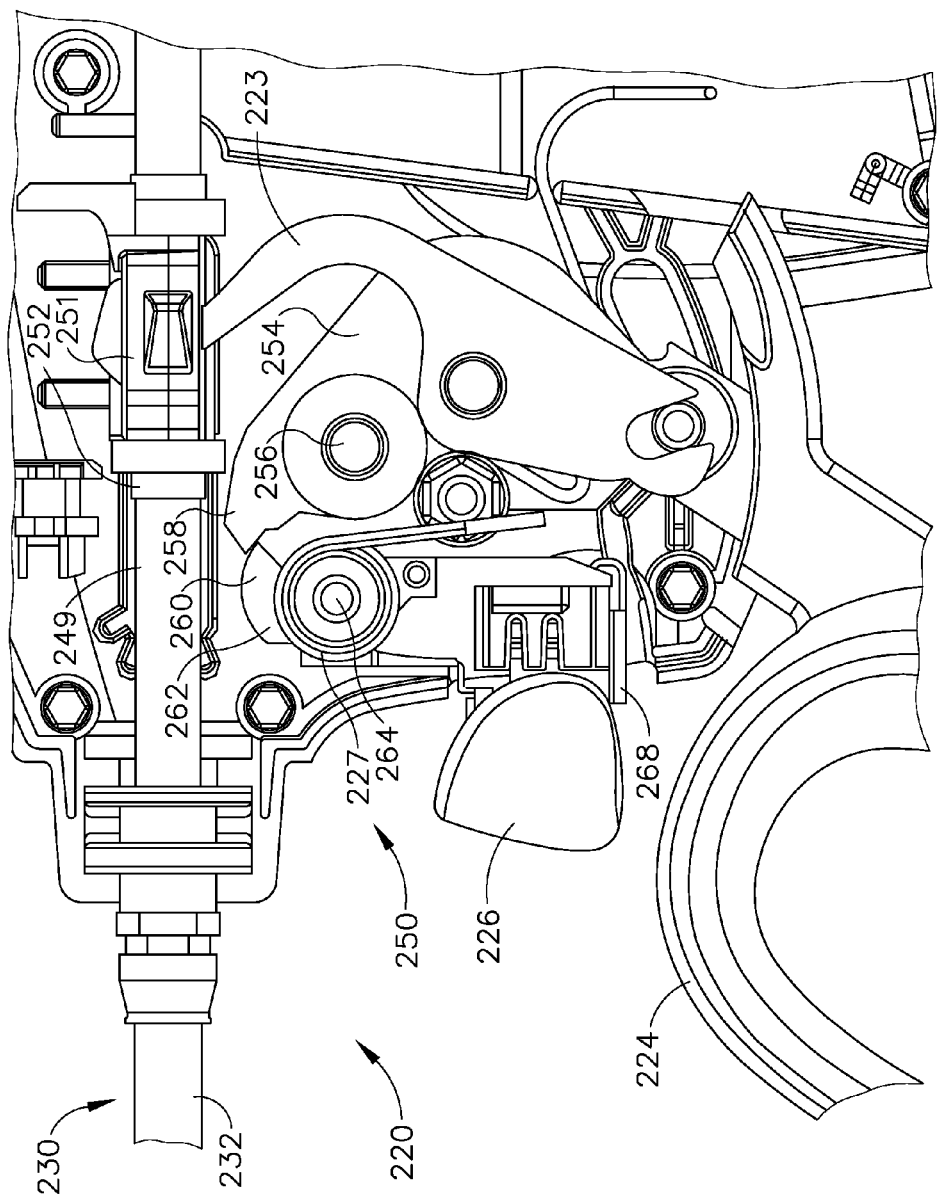

ELECTROSURGICAL INSTRUMENT WITH MULTI-STAGE ACTUATOR

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011(now U.S. Pat. No. 8,939,974, issued Jan. 27, 2015), the disclosure of which is incorporated by reference herein; U.S. Pub. No. 2012/0083783 (now U.S. Pat. No. 8,888,809), entitled "Surgical Instrument with Jaw Member," published Apr. 5, 2012, the disclosure of which is incorporated by reference herein; U.S. Pub. No. 2012/0116379, entitled "Motor Driven Electrosurgical Device with Mechanical and Electrical Feedback," published May 10, 2012 (now U.S. Pat. No. 9,161,803, issued Oct. 20, 2015), the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247 (pending), entitled "Articulation Joint Features for Articulating Surgical Device," published Mar. 29, 2012, the disclosure of which is incorporated by reference herein; U.S. Pub. No. 2013/0030428, entitled "Surgical Instrument with Multi-Phase Trigger Bias," published Jan. 31, 2013 (now U.S. Pat. No. 9,089,327, issued Jul. 28, 2015), the disclosure of which is incorporated by reference herein; and U.S. Pub. No. 2013/0023868 (pending), entitled "Surgical Instrument with Contained Dual Helix Actuator Assembly," published Jan. 31, 2013, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 10 depicts a side view of an exemplary alternative handpiece suitable for incorporation with the instrument of FIG. 1, with an exemplary alternative lockout mechanism;

Figure 1:
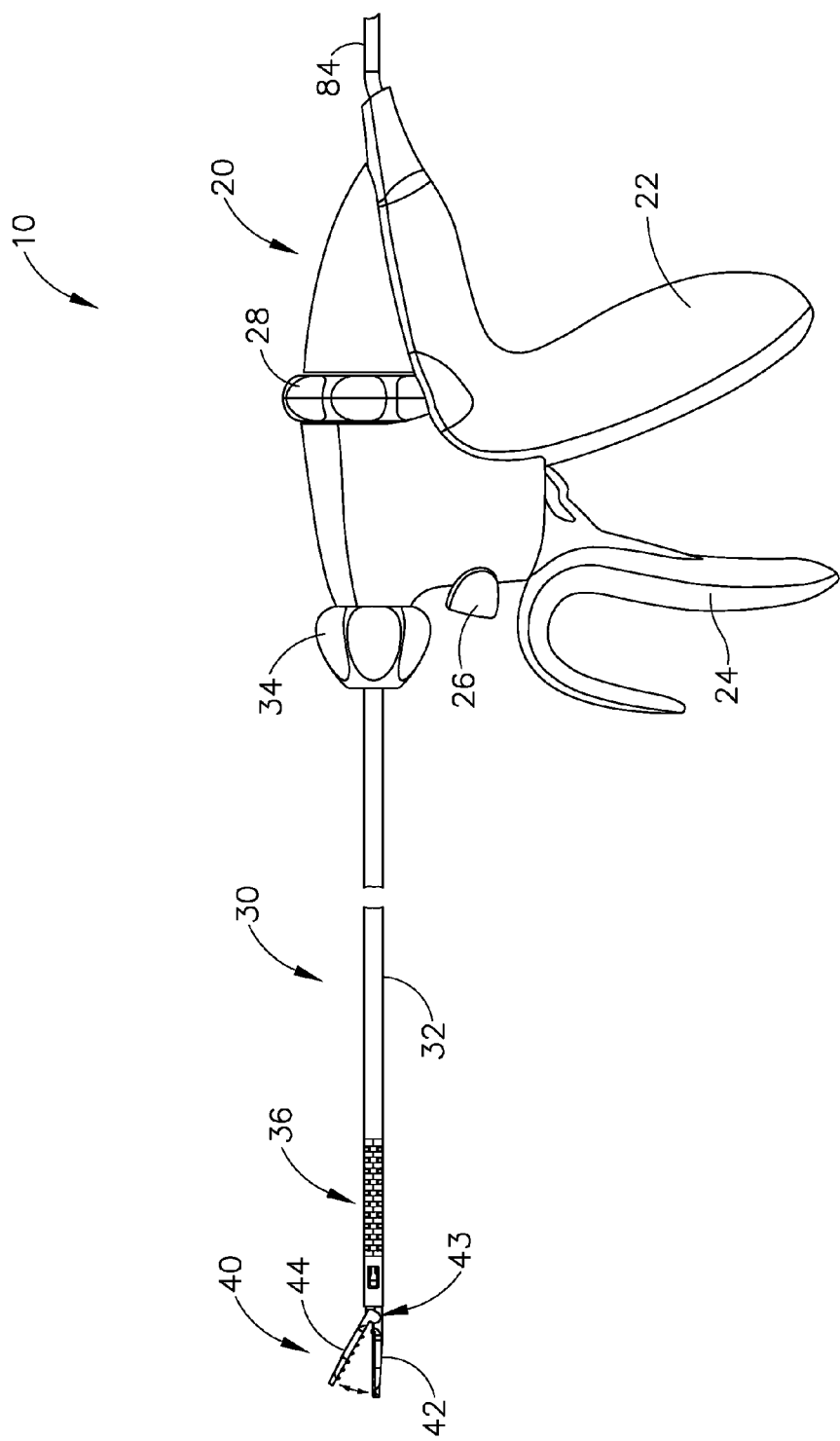
FIG. 1 depicts a side elevational view of an exemplary electrosurgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218 (now U.S. Pat. No. 8,939,974); U.S. Pub. No. 2012/0083783; (now U.S. Pat. No. 8,888,809); U.S. Pub. No. 2012/0116379 (now U.S. Pat. No. 9,161,803); U.S. Pub. No. 2012/0078243 (pending); U.S. Pub. No. 2012/0078247 (pending); U.S. Pub. No. 2013/0030428 (now U.S. Pat. No. 9,089,327); and/or U.S. Pub. No. 2013/0023868 (pending). As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247 (pending), the disclosure of which is incorporated by reference herein. As another merely illustrative example, articulation section (36) may be configured in accordance with one or more teachings of U.S. Pub. No. 2012/0078248 (pending), entitled "Articulation Joint Features for Articulating Surgical Device," published Mar. 29, 2012, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively laterally deflect end effector (40) at various angles relative to the longitudinal axis defined by shaft (30). While articulation control (28) is in the form of a rotary dial in the present example, it should be understood that articulation control (28) may take numerous other forms. By way of example only, some merely illustrative forms that articulation control (28) and other components of handpiece (20) may take are disclosed in U.S. Pub. No. 2012/0078243 (pending), the disclosure of which is incorporated by reference herein; in U.S. Pub. No. 2012/0078244 (pending), entitled "Control Features for Articulating Surgical Device," published Mar. 29, 2012, the disclosure of which is incorporated by reference herein; and in U.S. Pub. No. 2013/0023868 (pending), the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
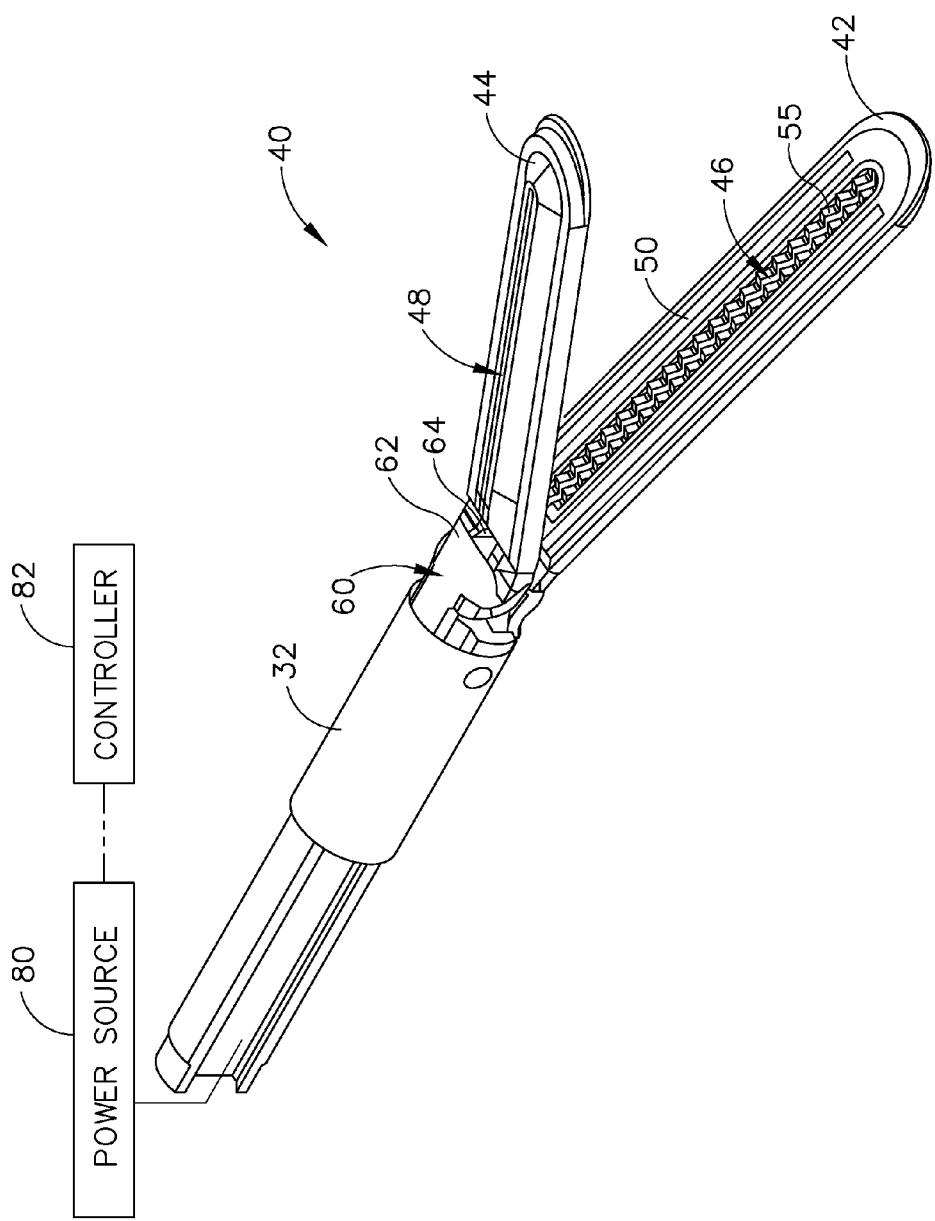
FIG. 2 depicts a perspective view of the end effector of the instrument of FIG. 1, in an open configuration.
Figure 3:
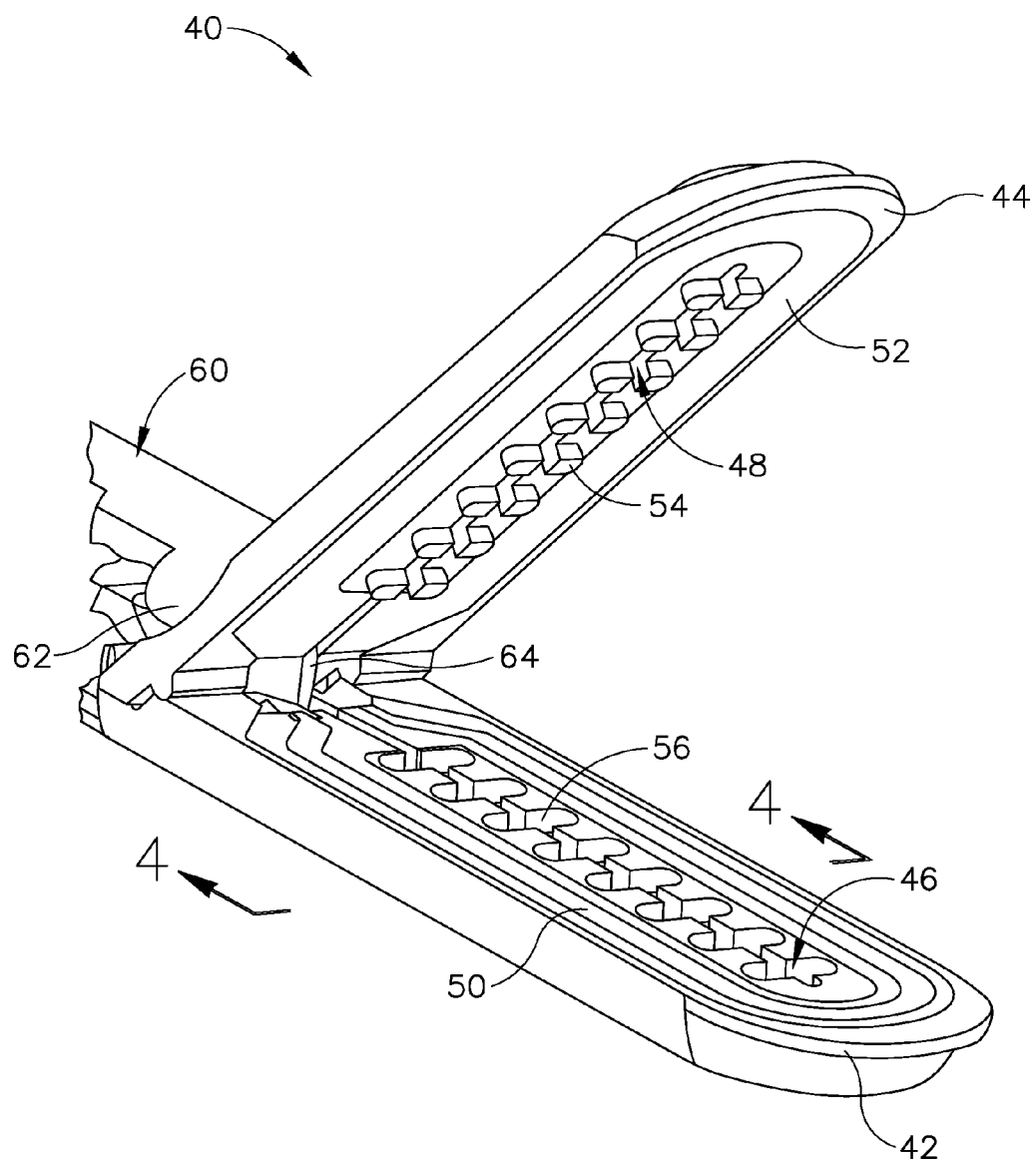
FIG. 3 depicts another perspective view of the end effector of the instrument of FIG. 1, in an open configuration.
Figure 4:
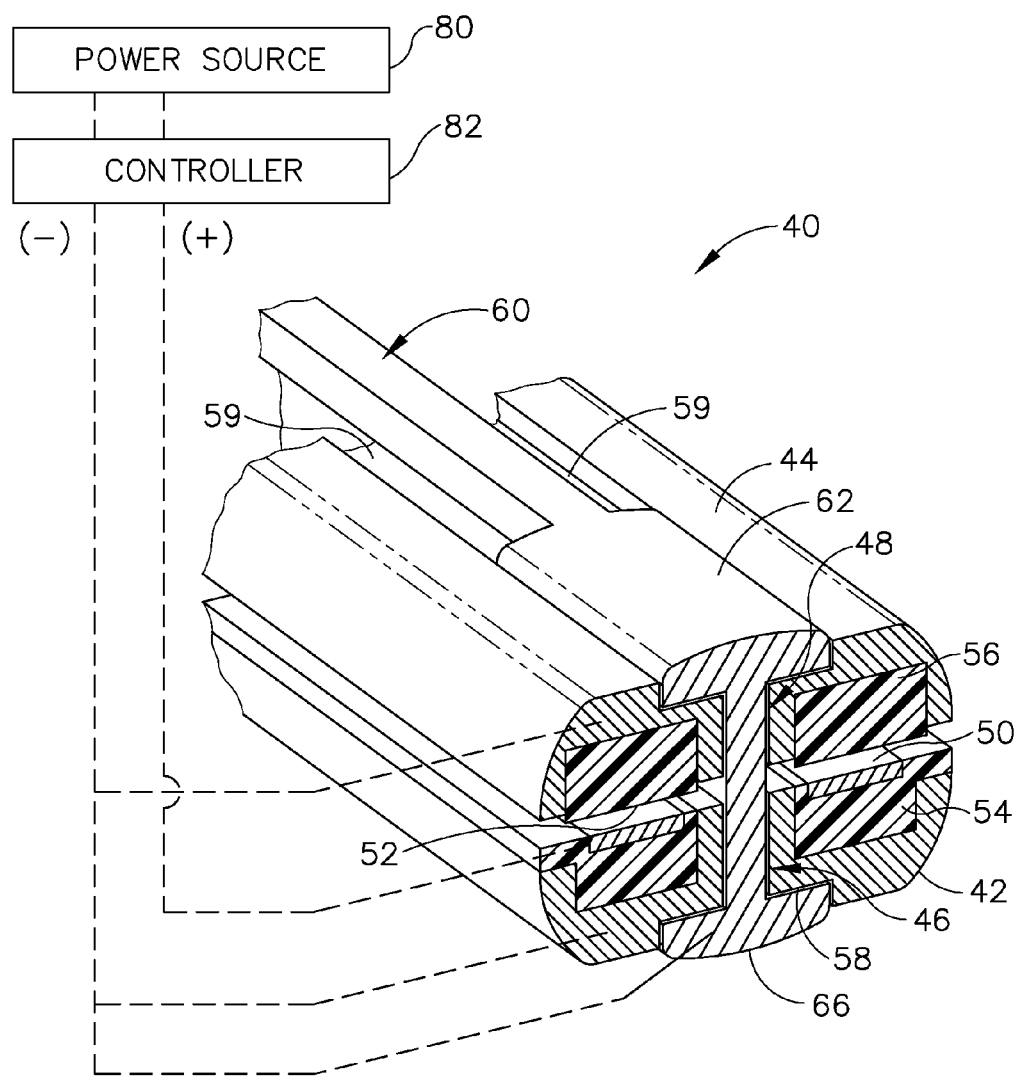
FIG. 4 depicts a cross-sectional end view of the end effector of FIG. 2, in a closed configuration and with the blade in a distal position, taken along line 4-4 of FIG. 3.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44).

Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768 (expired), entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011 (now U.S. Pat. No. 9,089,360, issued Jul. 28, 2015), the disclosure of which is incorporated by reference herein; U.S. Pub. No. 2011/0087212 , entitled "Surgical Generator for Ultrasonic and Electrosurgical Devices," published Apr. 14, 2011 (now U.S. Pat. No. 8,986, 302, issued Mar. 24, 2015), the disclosure of which is incorporated by reference herein; U.S. Pub. No. 2011/0087213, entitled "Surgical Generator for Ultrasonic and Electrosurgical Devices," published Apr. 14, 2011 (now U.S. Pat. No. 8,951,248, issued Feb. 10, 2015), the disclosure of which is incorporated by reference herein; U.S. Pub. No. 2011/0087214, entitled "Surgical Generator for Ultrasonic and Electrosurgical Devices," published Apr. 14, 2011 (now U.S. Pat. No. 9,039,695, issued May 26, 2015), the disclosure of which is incorporated by reference herein; U.S. Pub. No. 2011/0087215, entitled "Surgical Generator for Ultrasonic and Electrosurgical Devices," published Apr. 14, 2011 (now U.S. Pat. No. 9,050,093, issued Jun. 9, 2015), the disclosure of which is incorporated by reference herein; U.S. Pub. No. 2011/0087216, entitled "Surgical Generator for Ultrasonic and Electrosurgical Devices," published Apr. 14, 2011 (now U.S. Pat. No. 8,956,349, issued Feb. 17, 2015), the disclosure of which is incorporated by reference herein; and/or U.S. Pub. No. 2011/0087217, entitled "Surgical Generator for Ultrasonic and Electrosurgical Devices," published Apr. 14, 2011 (now U.S. Pat. No. 9,060,776, issued Jun. 23, 2015), the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. In other words, it should be understood that serrations may be generally blunt or otherwise atraumatic. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60)

remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

Figure 5:
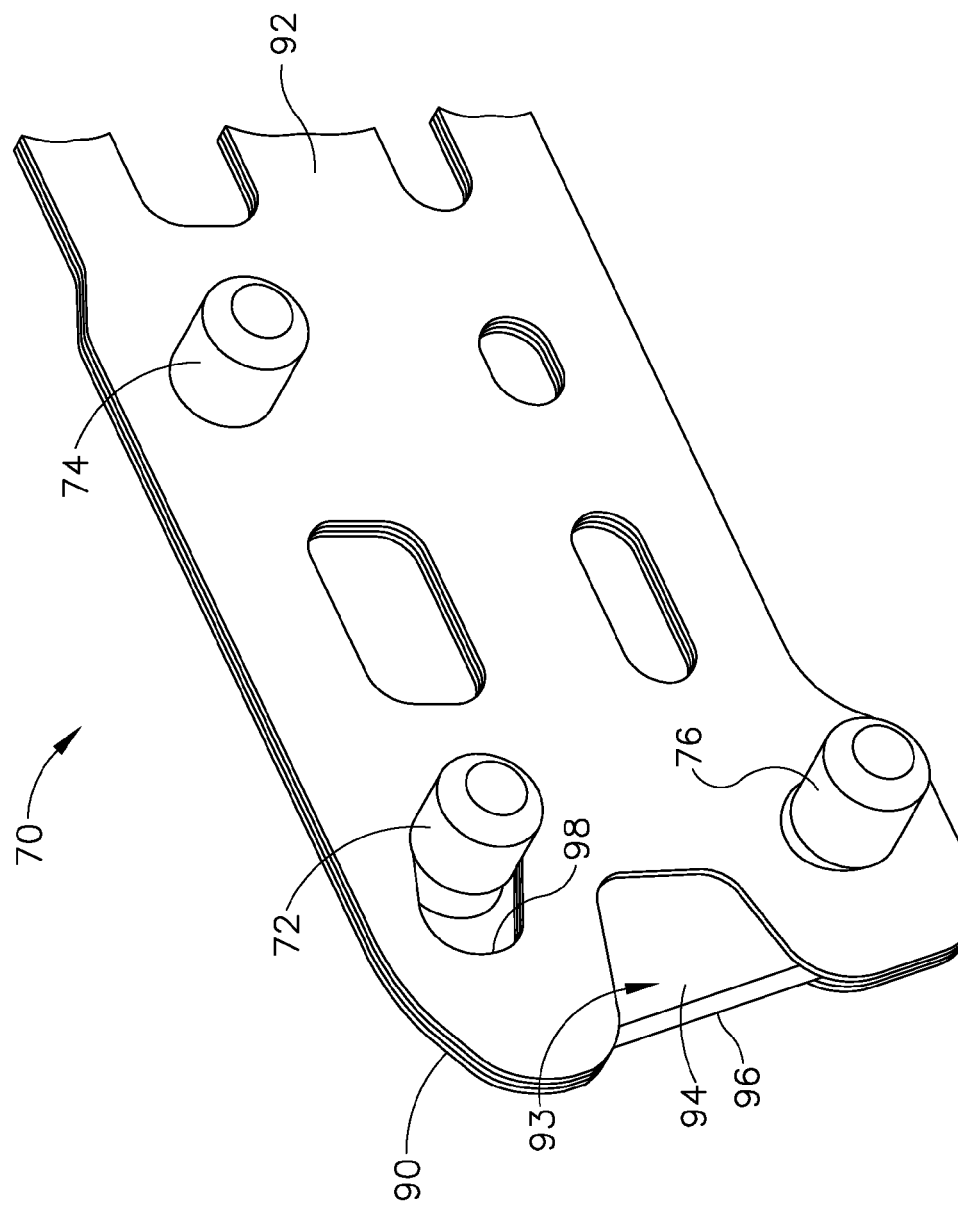
FIG. 5 depicts a partial perspective view of the distal end of an exemplary alternative firing beam suitable for incorporation in the instrument of FIG. 1.

FIG. 5 shows an exemplary alternative firing beam (70), which may be readily substituted for firing beam (60). In this example, firing beam (70) comprises a blade insert (94) that is interposed between two beam plates (90, 92). Blade insert (94) includes a sharp distal edge (96), such that blade insert (94) will readily sever tissue that is captured between jaws (42, 44). Sharp distal edge (96) is exposed by a proximally extending recess (93) formed in plates (90, 92). A set of pins (72, 74, 76) are transversely disposed in plates (90, 92). Pins (72, 74) together effectively serve as substitutes for upper flange (62); while pin (76) effectively serves as a substitute for lower flange (66). Thus, pins (72, 74) bear against channel (59) of jaw (44), and pin (76) bears against channel (58) of jaw (42), as firing beam (70) is translated distally through slots (46, 48). Pins (72, 74, 76) of the present example are further configured to rotate within plates (90, 92), about the axes respectively defined by pins (72, 74, 76). It should be understood that such rotatability of pins (72, 74, 76) may provide reduced friction with jaws (42, 44), thereby reducing the force required to translate firing beam (70) distally and proximally in jaws (42, 44). Pin (72) is disposed in an angled elongate slot (98) formed through plates (90, 92), such that pin (72) is translatable along slot (98). In particular, pin (72) is disposed in the proximal portion of slot (98) as firing beam (70) is being translated distally. When firing beam (70) is translated proximally, pin (72) slides distally and upwardly in slot (98), increasing the vertical separation between pins (72, 76), which in turn reduces the compressive forces applied by jaws (42, 44) and thereby reduces the force required to retract firing beam (70). Of course, firing beam (70) may have any other suitable configuration. By way of example only, firing beam (70) may be configured in accordance with at least some of the teachings of U.S. Pub. No. 2012/0083783 (now U.S. Pat. No. 8,888,809), the disclosure of which is incorporated by reference herein.

D. Exemplary Operation

In an exemplary use, end effector (40) is inserted into a patient via a trocar.

Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument

(10) may be operable and operated will be apparent to those of ordinary skill in the art in view of the teachings herein.

II. Exemplary Lockout Mechanism

It should be understood from the foregoing that, as firing beam (60) is advanced through a first range of motion, firing beam (60) causes jaws (42, 44) to clamp tissue without severing the tissue; and as firing beam (60) continues to advance through a second range of motion following the first range of motion, firing beam (60) severs the tissue clamped between jaws (42, 44). In some instances, it may be desirable to activate electrode surfaces (50, 52) to initiate sealing of clamped tissue before firing beam (60) advances through the second range of motion. However, even if the operator wishes to seal the tissue, the operator may fail to fully depress button (26) to activate electrode surfaces (50, 52) before driving firing beam (60) through the second range of motion, resulting of cutting non-sealed tissue. Furthermore, an operator may wish to use end effector (40) to simply grasp and seal tissue with jaws (42, 44), without severing the tissue at all. In any of these scenarios (among others), it may be desirable to provide a lockout that provides staged actuation of trigger (24), such that movement of trigger (24) is arrested upon completion of the first range of motion without button (26) being adequately depressed. Similarly, it may be desirable to provide a lockout where trigger (24) cannot be pivoted toward grip (22) until button (26) is being adequately depressed. The following description relates to merely illustrative examples of lockout features that selectively restrict movement of trigger (24).

A. Exemplary Lockout Mechanism Directly Restricting Distal Motion

Figure 6:
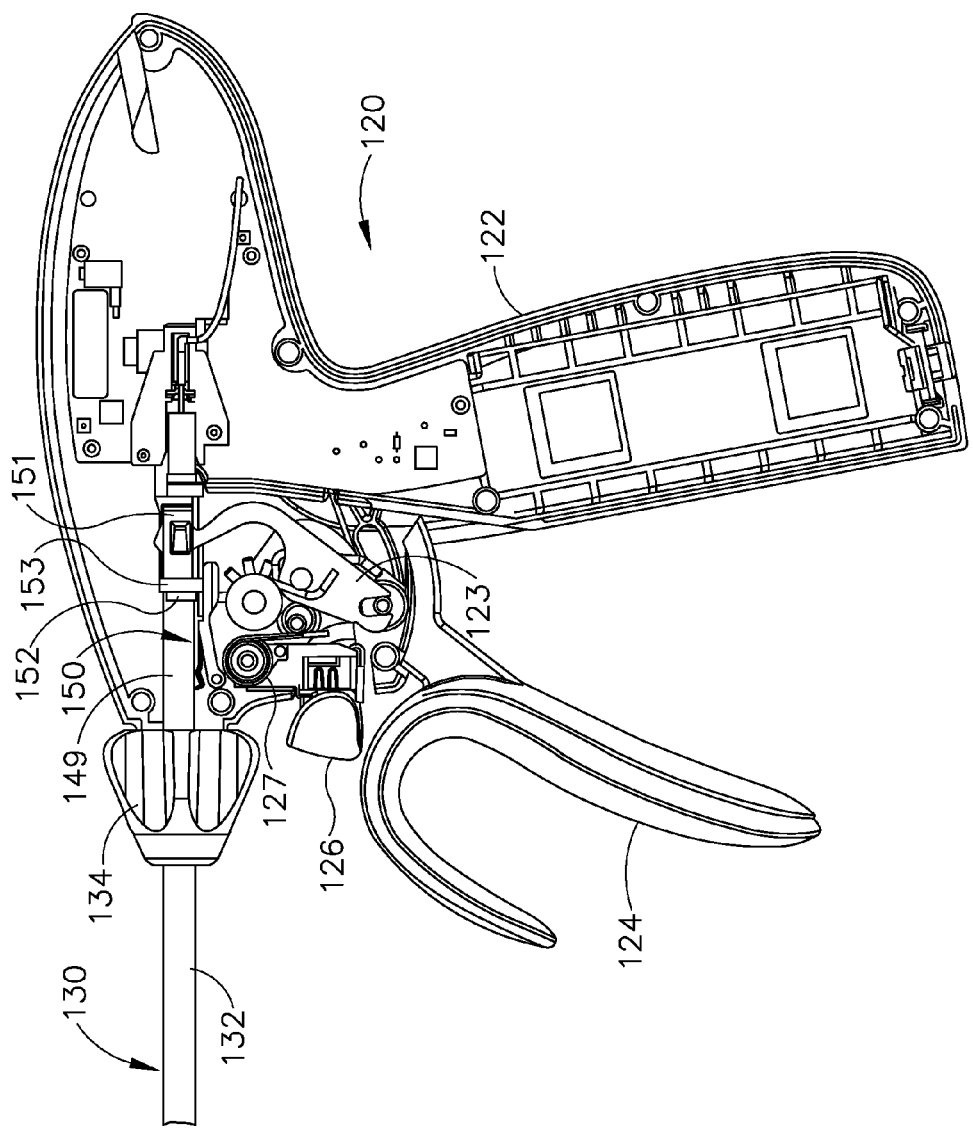
FIG. 6 depicts a side view of an exemplary alternative handpiece suitable for incorporation with the instrument of FIG. 1, with a housing half removed.

FIG. 6 shows an exemplary handpiece (120) that may be readily incorporated into instrument (10). A shaft (130) extends distally from handpiece (120). Shaft (130) may be configured substantially similar to (30), including having an articulation section (36) and end effector (40), etc. Shaft (130) comprises a rigid outer sheath (132) substantially similar to sheath (32) described above. A knob (134) is positioned at the proximal end of shaft (130) and is operable to rotate outer sheath (132) relative to handpiece (120) in a substantially similar manner to knob (34) described above. Handpiece (120) comprises a pistol grip (122), a pivoting trigger (124), and an activation button (126). Pistol grip (122), pivoting trigger (124), and activation button (126) are substantially similar to pistol grip (22), pivoting trigger (24), and activation button (26) described above. It will be understood that handpiece (120) also has a housing cover (not shown) configured to enclose the components within handpiece (120). However, for visualization purposes, such a housing cover is not shown.

Figure 7:
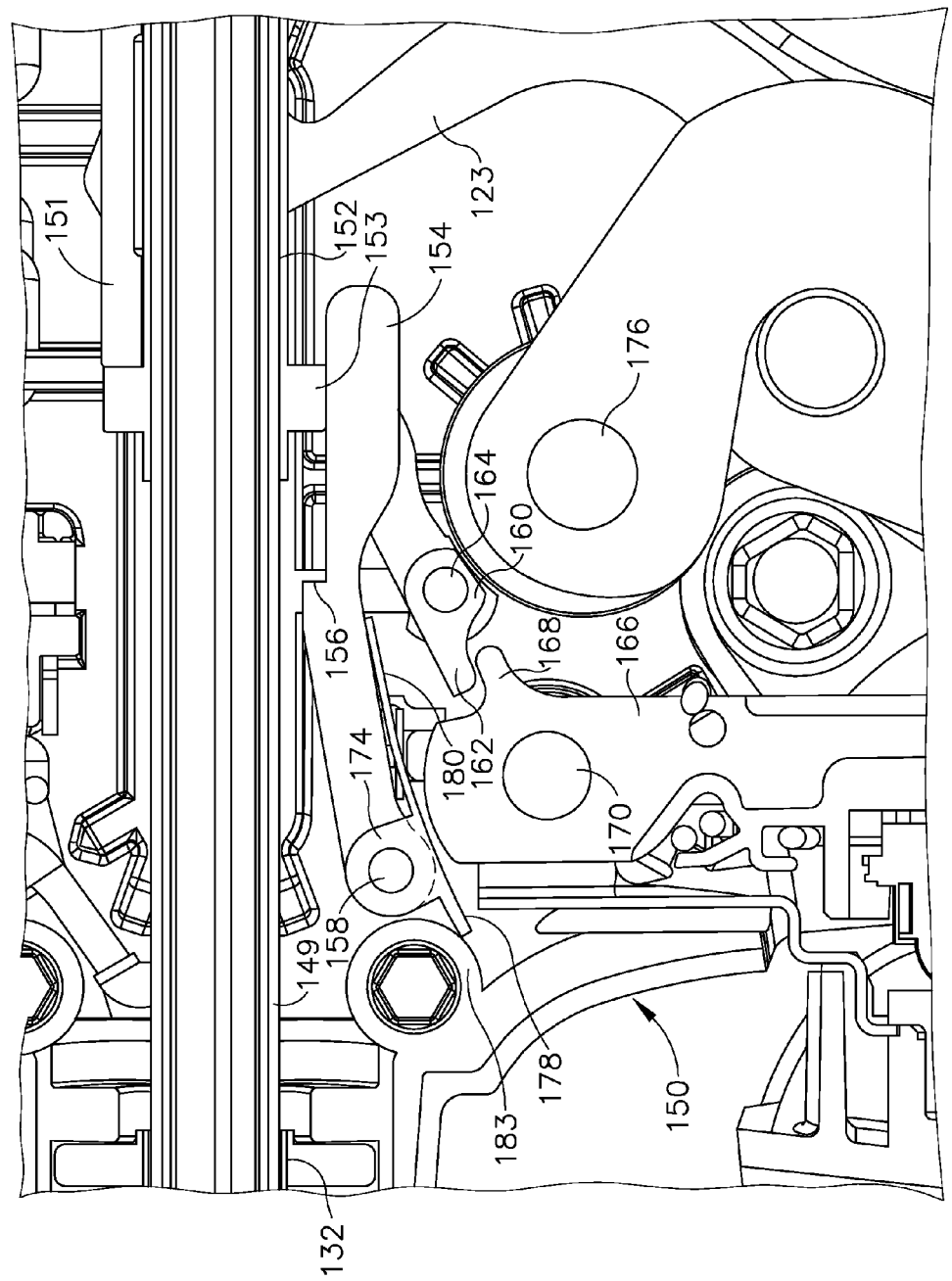
FIG. 7 depicts an enlarged side elevation view of the handpiece of FIG. 1 depicting an exemplary lockout mechanism.

A firing tube (149) is slidably disposed in outer sheath (132) and extends proximally into handpiece (120). The distal end of firing tube (149) is secured to a firing beam like firing beam (60) described above, which is operable to close the jaws of an end effector and drive a distal blade through the end effector. A drive spool (152) (best seen in FIG. 7) is unitarily secured to firing tube (149) such that drive spool (152) and firing tube (149) translate unitarily relative to outer sheath (132) and relative to handpiece (120). Drive spool (152) is partially surrounded by a driver block (151), which is configured to translate with drive spool (152) yet permits drive spool (152) and firing tube (149) to rotate relative to driver block (151). Trigger (124) is coupled with driver block (151) through a trigger link (123). Trigger link (123) engages driver block (151) such that when the user pivots pivoting trigger (124) toward grip (122), trigger link (123) distally advances driver block (151) and drive spool (152), thereby advancing firing tube (149) and the firing beam. Thus, pulling trigger (124) toward grip (122) advances the firing beam.

Handpiece (120) of the present example further comprises a lockout mechanism (150). Lockout mechanism (150) is operable to selectively restrict advancement of the firing beam. In particular, lockout mechanism (150) is configured to block the translation of drive spool (152) relative to shaft (130) such that the firing beam cannot translate distally until lockout mechanism (150) is unlocked. FIGS. 7-9B show lockout mechanism (150) in greater detail. Lockout mechanism (150) comprises a lockout arm (154), a lockout lever (166), a linking arm (160), and a lockout spring (174). Lockout arm (154) is operable to selectively block the translation of drive spool (152); while lockout lever (166), linking arm (160), and lockout spring (174) cooperatively engage and disengage lockout arm (154) from drive spool (152).

Lockout arm (154) is pivotally coupled in handpiece (120) by a pin (158), which extends through both lockout arm (154) and lockout spring (174). Lockout arm (154) is configured to pivot about pin (158). Lockout arm (154) includes a proximally presented shoulder (156) operable to engage a distal annular flange (153) of drive spool (152). In particular, in the position shown in FIG. 9A (where driver block (151) is omitted for clarity), shoulder (156) is operable to block the translation of drive spool (152) by physically blocking annular flange (153). However, shoulder (156) is positioned to allow drive spool (152) to translate through a first range of motion, as can be seen from the transition between the positioning shown in FIGS. 7-8 and the positioning shown in FIG. 9A. It should be understood that, as drive spool (152) translates through this first range of motion, firing tube (149) and the firing tube also translate through a first range of motion. This first range of motion may be the same as the first range of motion referred to above, where jaws of an end effector at the distal end of shaft (130) clamp tissue but before a distal blade of the firing beam severs tissue clamped between the jaws.

Lockout spring (174) has a first end (178) and a second end (180). First end (178) is pressed against a rib (183) within handpiece (120). It will be appreciated that rib (183) prevents lockout spring (174) from rotating about arm pin (158) beyond the position of rib (183). Second end (180) contacts lockout arm (154) and is operable to apply an upward bias such that lockout arm (154) is biased to be in the position shown in FIGS. 7-9A. By way of example only, lockout spring (174) may be formed of metal or some other resilient material.

Figure 8:
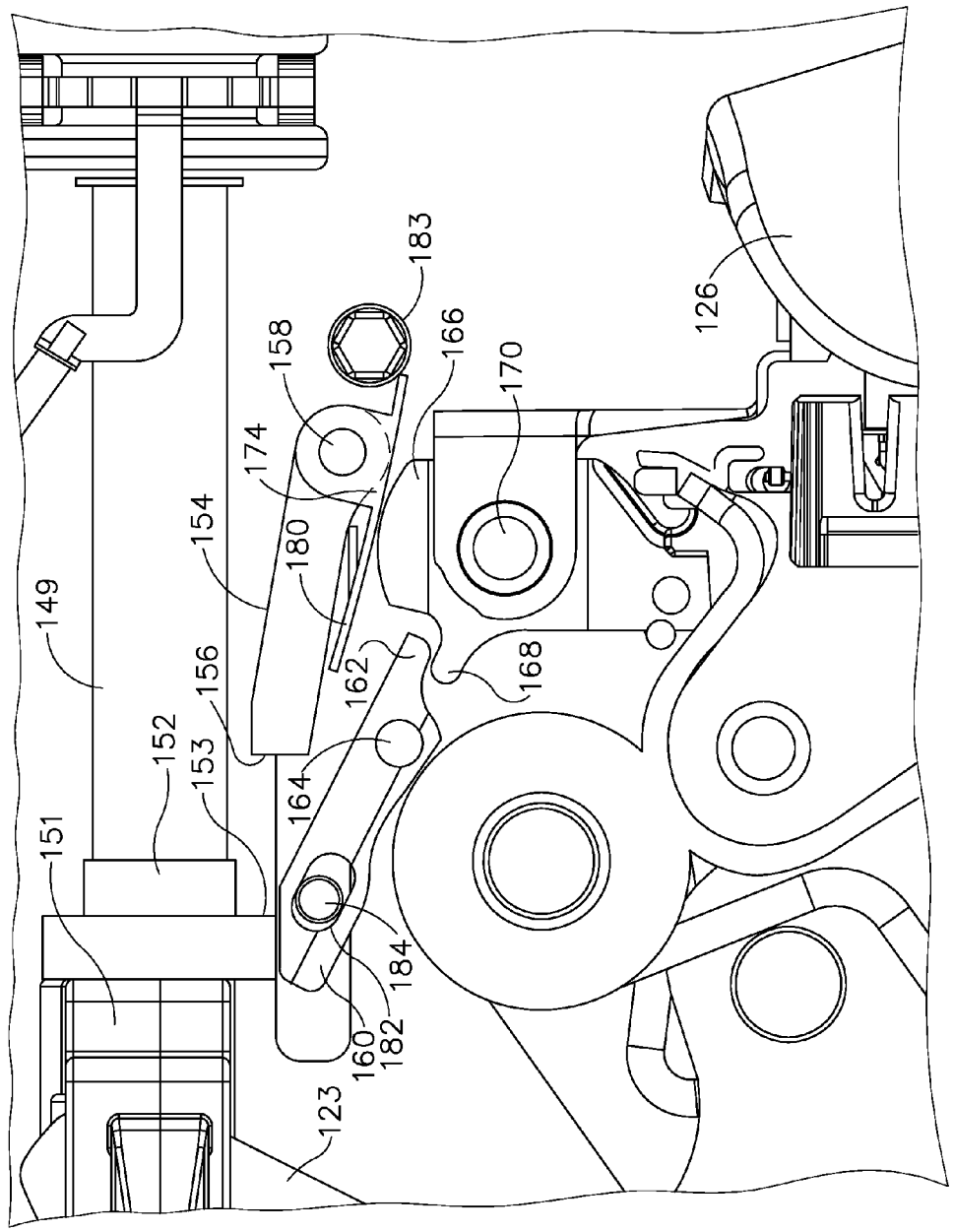
FIG. 8 depicts an enlarged side elevation view of the lockout mechanism of FIG. 7 from the opposite side shown in FIG. 7.

Lockout arm (154) is in communication with linking arm (160). Linking arm (160) comprises a protrusion (162) operable to engage lockout lever (166). A link pin (164) extends through linking arm (160), thereby allowing linking arm (160) to pivot about link pin (164). As seen in FIG. 8, which shows the other side of linking arm (160), linking arm (160) defines an elongate linking slot (182). Lockout arm (154) comprises a slot pin (184) that extends transversely through linking slot (182). In one dimension, linking slot (182) has approximately the same diameter as linking pin (184), though in another dimension, linking slot (182) is substantially longer than the diameter of slot pin (184). As linking arm (160) pivots about link pin (164), linking arm (160) urges slot pin (184) to slide along linking slot (182), thereby causing lockout arm (154) to pivot about arm pin (158). In particular, as protrusion (162) pivots upwardly about pin (164), the other end of linking arm (160) pulls lockout arm (154) downwardly via pin (184), such that lockout arm (154) pivots downwardly about pin (158). When lockout arm (154) pivots upwardly about pin (158), pin (184) causes linking arm (160) to pivot about pin (164).

Lockout lever (166) comprises a lever arm (168). Lever arm (168) has a rounded shape and is operable to engage protrusion (162). Lockout lever (166) is pivotable about a lever pin (170). In particular, when activation button (126) is pressed, lockout lever (166) pivots about pin (170) such that lever arm (168) presses upwardly against protrusion (162). Protrusion (162) then moves upwardly, which pivots linking arm (160) about link pin (164), which then pulls lockout arm (154) downwardly. At the end of this sequence, it will be appreciated that lockout arm (154) has pivoted downwardly low enough such that shoulder (156) no longer blocks movement of flange (153). Thus, drive spool (152) can advance longitudinally past shoulder (156).

Figure 9A:
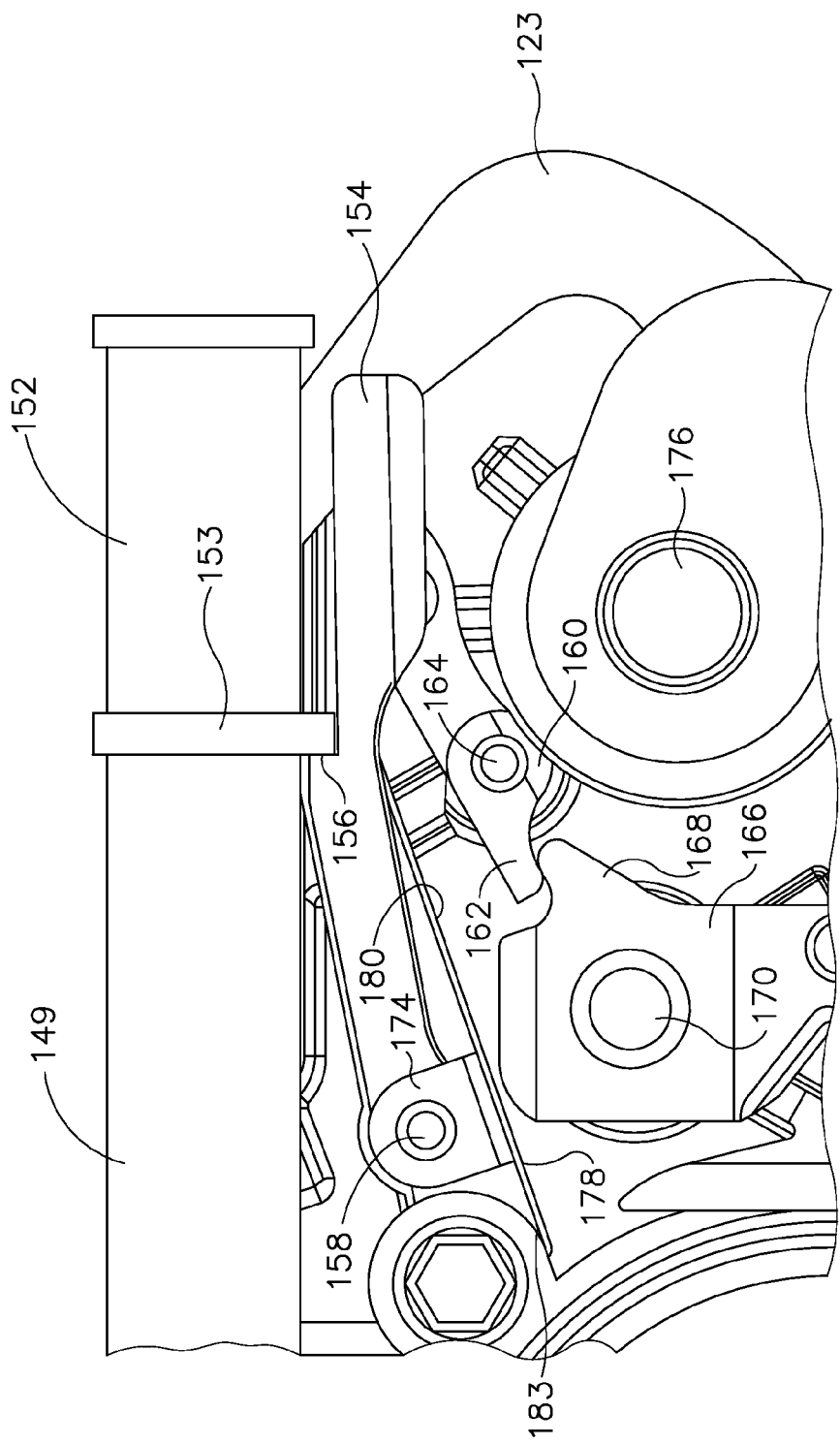
FIG. 9A depicts a side elevation view of the lockout mechanism of FIG. 7 in a first position.
Figure 9B:
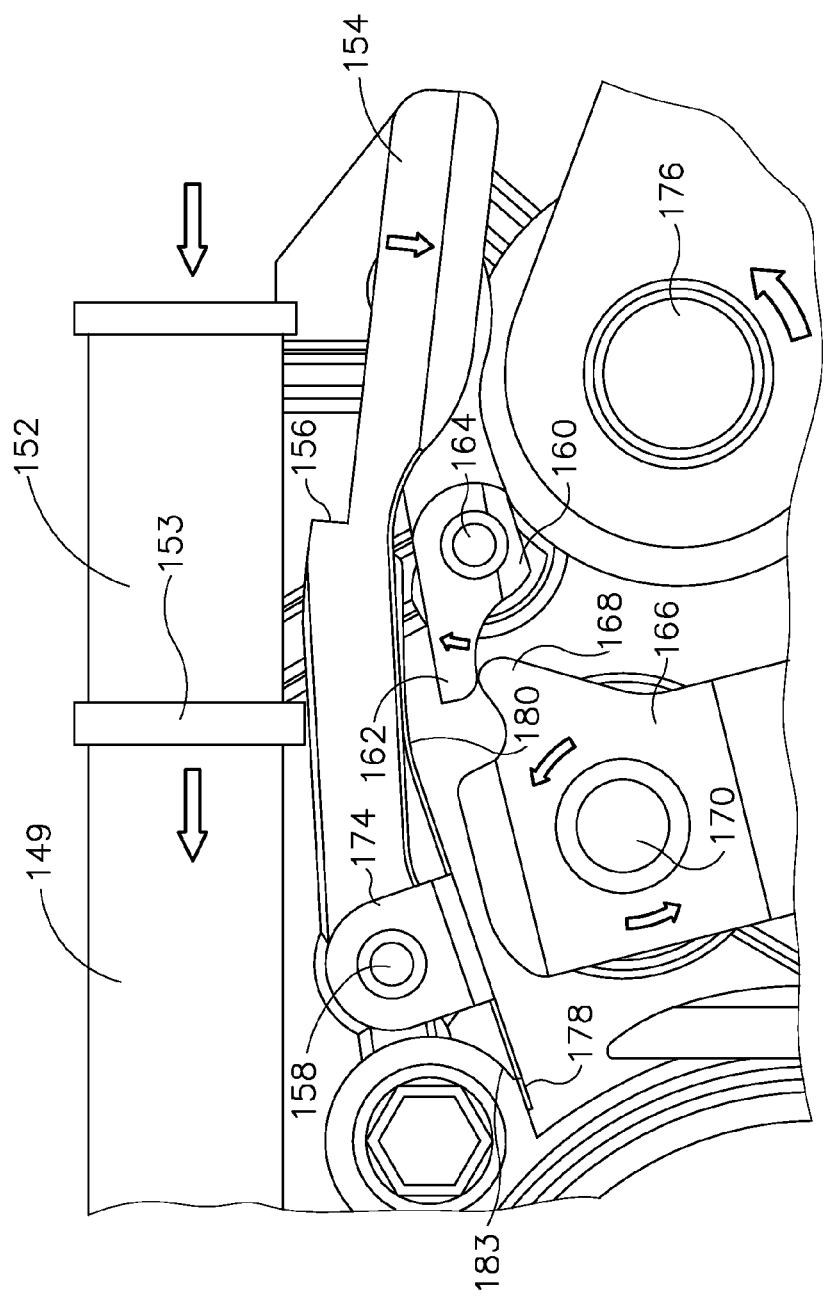
FIG. 9B depicts a side elevation view of the lockout mechanism of FIG. 7 in a second position.

FIGS. 9A-9B show an exemplary movement of lockout mechanism (150). FIG. 9A shows lockout mechanism (150) in a "home" position, with driver block (151) omitted for clarity. In this home position, lockout spring (174) is straight in an unbent position and biases lockout arm (154) to an upper position, which prevents longitudinal motion of drive spool (152) beyond proximally presented shoulder (156). It will be appreciated that by assuming the position shown in FIG. 9A, the instrument that incorporates handpiece (120) will not sever tissue clamped between the jaws of an end effector. Thus, pulling on pivoting trigger (124) will only allow drive spool (152) to hit proximally presented shoulder (156), which may close the jaws of an end effector about tissue; but not allow a firing beam to advance a distal blade to sever the tissue.

When the operator wishes to "unlock" handpiece (120) such that the instrument incorporating handpiece (120) can fully fire, user can depress activation button (126). As seen in FIG. 6, activation button (126) is biased by a button spring (127) to assume the position in FIG. 6. Returning to FIG. 9A, the user can overcome the bias by pressing activation button (126). This may activate electrode surfaces in the end effector with RF energy as described above. In addition, this pressing of activation button (126), pivots lockout lever (166) about lever pin (170), causing lever arm (168) to urge protrusion (162) upwardly. Linking arm (160) then pulls lockout arm (154) downwardly. Lockout spring (174) bends as seen in FIG. 9B in order to allow lockout arm (154) to lower as seen in the illustrated version. Consequently, lockout arm (154) lowers sufficiently to allow drive spool (152) to longitudinally advance beyond shoulder (156) in response to the user pulling pivoting trigger (124). As drive spool (152) advances, so does firing tube (149) and the firing beam that is secured to firing tube (149). As a result, pulling pivoting trigger (124) with activation button (126) depressed allows a user to fully fire the instrument that incorporates handpiece (120). Again, driver block (151) is omitted from FIG. 9B for clarity.

When activation button (126) is released, the spring bias of button spring (127) and lockout spring (174) return lockout mechanism (150) to the position shown in FIG. 9A. In particular, lockout spring (174) pushes lockout arm (154) upwardly and button spring (127) pushes activation button (126) away from handpiece (120). As the operator relaxes their grip on trigger (124) and allows trigger (124) to pivot away from pistol grip (122), the firing beam, firing tube (149), and drive spool (152) all retract proximally, such that flange (153) of drive spool (152) is eventually positioned proximal to shoulder (156). The above actuation, unlocking, and relocking sequences may be repeated as many times as desired.

B. Exemplary Lockout Mechanism Directly Restricting Pivotal Motion

FIG. 10 shows another exemplary lockout mechanism (250) incorporated into a handpiece (220). It will be appreciated that lockout mechanism (250) may be incorporated into a surgical instrument such as instrument (10) and/or any other suitable suitable surgical instrument. While lockout mechanism (150) is configured to prevent firing of a firing beam by impeding the longitudinal motion of drive spool (152), lockout mechanism (250) is operable to prevent firing of a firing beam by preventing actuation of a pivoting trigger (224). While lockout mechanisms (150, 250) may achieve similar results, they do so in substantially different ways.

Handpiece (220) of the present example is coupled with a shaft (230) having an outer tube (232). It will be appreciated that shaft (230) and outer tube (232) may be substantially similar to shafts (30, 130) and outer tubes (32, 132) described above. Handpiece (220) may also comprise features similar to knob (34, 134), pistol grip (22, 122), etc., described above. Handpiece (220) of the present example further comprises an activation button (226) and an RF switch (221). RF switch (221) is positioned just proximal to activation button (226) such that the operator may actuate RF switch (221) by pressing on activation button (226). When RF switch (221) is actuated, electrodes of the end effector at the distal end of shaft (230) are activated with RF energy to seal tissue clamped between jaws of the end effector, such as in the manner described above.

A firing tube (249) is slidably disposed in outer sheath (232) and extends proximally into handpiece (220). The distal end of firing tube (249) is secured to a firing beam like firing beam (60) described above, which is operable to close the jaws of an end effector and drive a distal blade through the end effector. A drive spool (252) is unitarily secured to firing tube (249) such that drive spool (252) and firing tube (249) translate unitarily relative to outer sheath (232) and relative to handpiece (220). Drive spool (252) is partially surrounded by a driver block (251), which is configured to translate with drive spool (252) yet permits drive spool (252) and firing tube (249) to rotate relative to driver block (251). Trigger (224) is coupled with driver block (251) through a trigger link (223). Trigger link (223) engages driver block (251) such that when the user pivots pivoting trigger (224) toward a grip (not shown), trigger link (223) distally advances driver block (251) and drive spool (252), thereby advancing firing tube (249) and the firing beam. Thus, pulling trigger (224) toward the grip advances the firing beam. It should be understood that trigger link (223) is intentionally omitted from FIGS. 11A-11D for clarity.

Lockout mechanism (250) of the present example is actuated by an activation button (226), which may be pressed by an operator. Lockout mechanism (250) further comprises tangs (266), which link activation button (226) with a lockout lever (262). Lockout lever (262) is secured within handpiece (220) by a trigger pin (264) and is operable to pivot about pin (264). Tangs (266) are mounted in handpiece (220) independently from lockout lever (262) and pin (264). Lockout lever (262) comprises a hook stopper (260) positioned above pin (264). Hook stopper (260) is shaped like a flat, curved, proximally oriented beak, though it will be appreciated that other suitable shapes may be used. Lockout lever (262) is spring biased to assume the position shown in FIGS. 10 and 11A by a torsion spring (227).

Lockout mechanism (250) is operable to selectively engage a distal projection (258) of a lockout arm (254). Lockout arm (254) is secured within handpiece (220) by an arm pin and is operable to pivot about pin (256). Distal projection (258) is configured rests on the top of hook stopper (260). Hook stopper (260) is configured to prevent distal projection (258) from rotating beyond hook stopper (260) when distal projection (258) is positioned on the top of hook stopper (260). Lockout arm (254) is coupled to trigger link (223) such that the user cannot actuate pivoting trigger (224) while hook stopper (260) blocks distal projection (258).

Figure 11A:
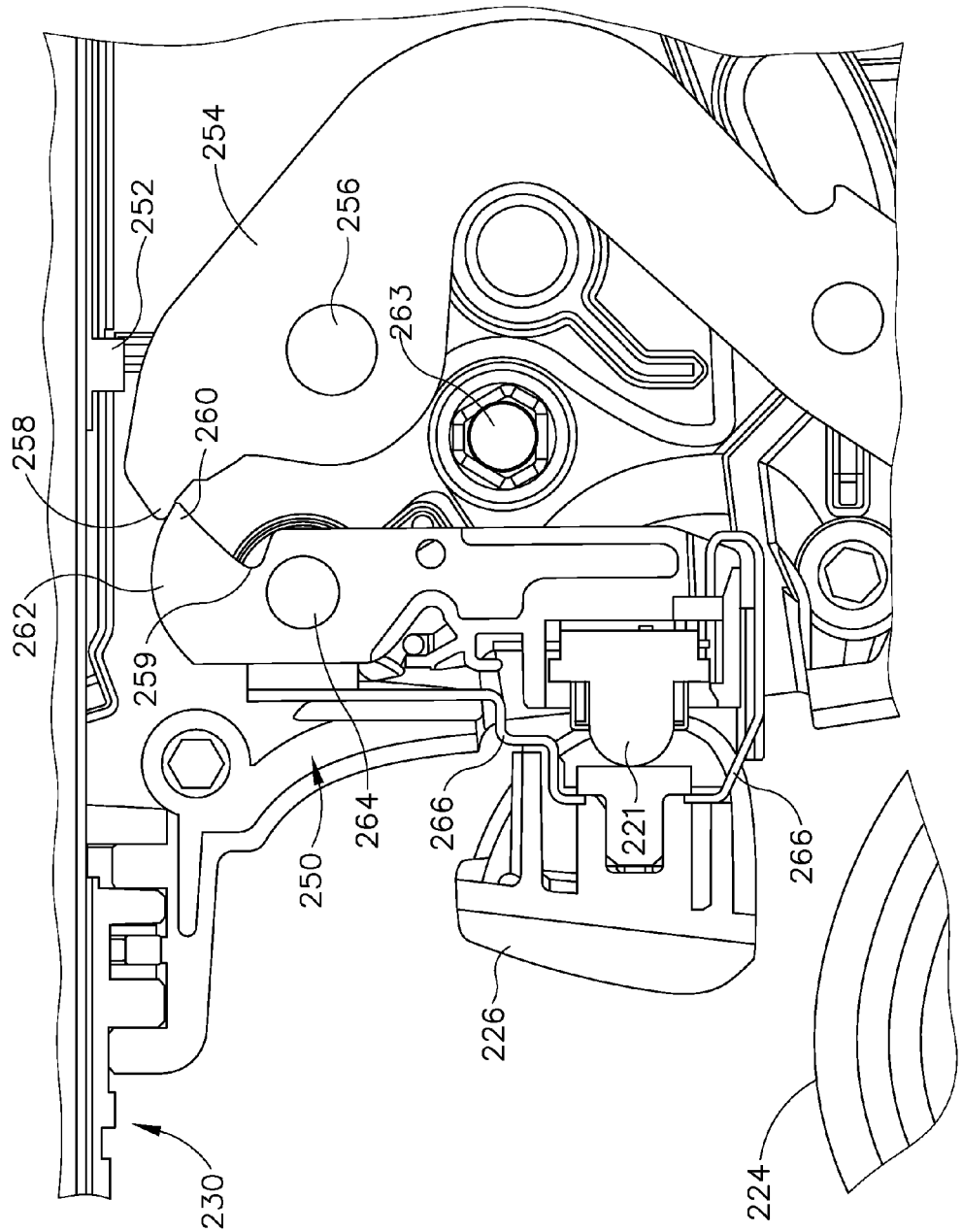
FIG. 11A depicts an enlarged side view of the lockout mechanism of FIG. 10 in a first position.
Figure 11B:
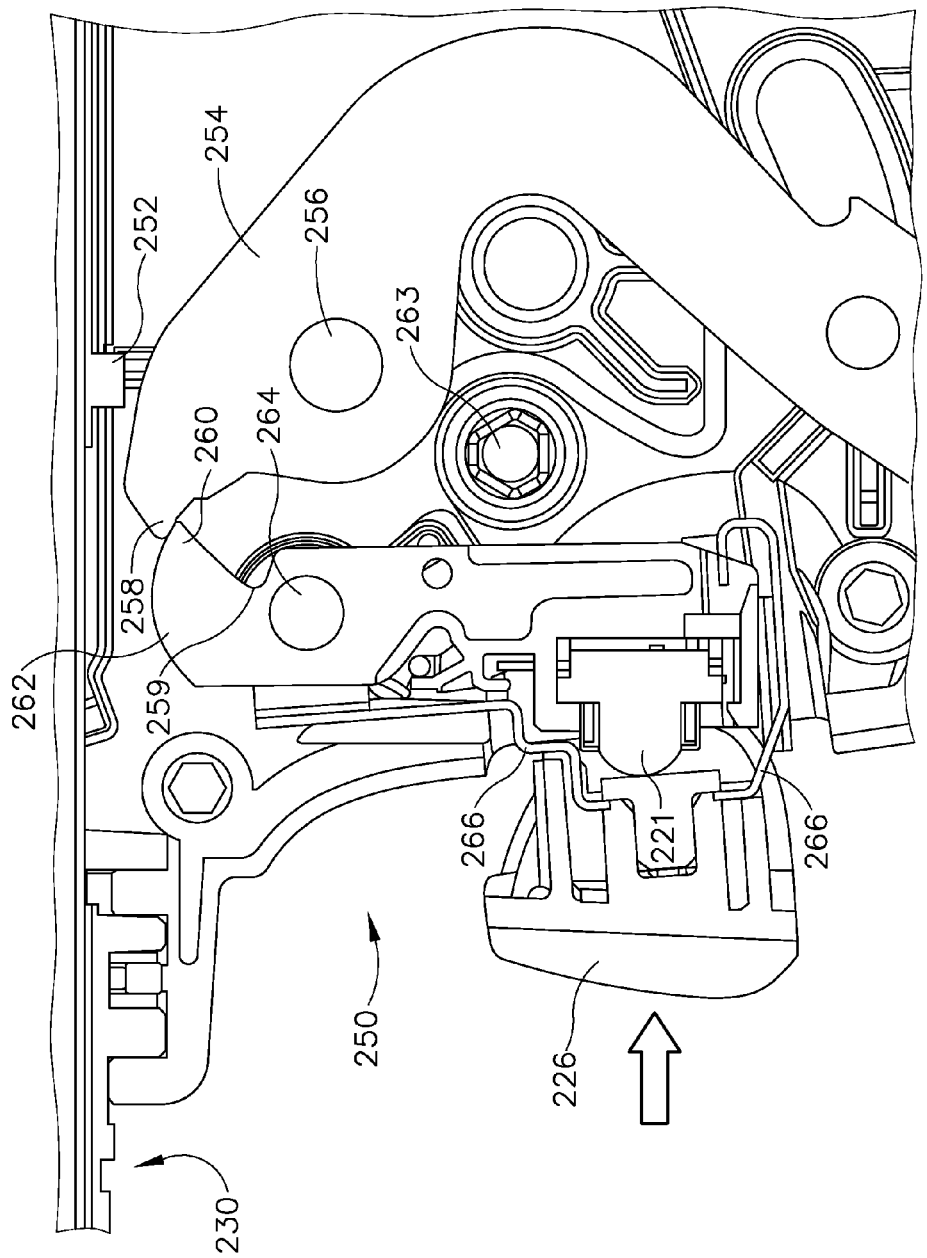
FIG. 11B depicts an enlarged side view of the lockout mechanism of FIG. 10 in a second position with the button partially depressed.

Activation button (226) may be pressed through two ranges of motion, with the first range resulting in a partial depress and the second range resulting in a full depress, which allows the user to fully actuate pivoting trigger (224). FIG. 11A shows lockout mechanism (250) with activation button (226) not depressed. At this stage, the electrodes of the end effector at the distal end of shaft (230) are not activated with RF energy. FIG. 11B shows activation button (226) in a partially depressed position. As shown, activation button (226) has actuated RF switch (221), thereby activating the electrodes of the end effector at the distal end of shaft (230) with RF energy. However, tangs (266) allow activation button (226) to be partially depressed without causing lockout lever (262) to pivot at this stage.

Figure 11C:
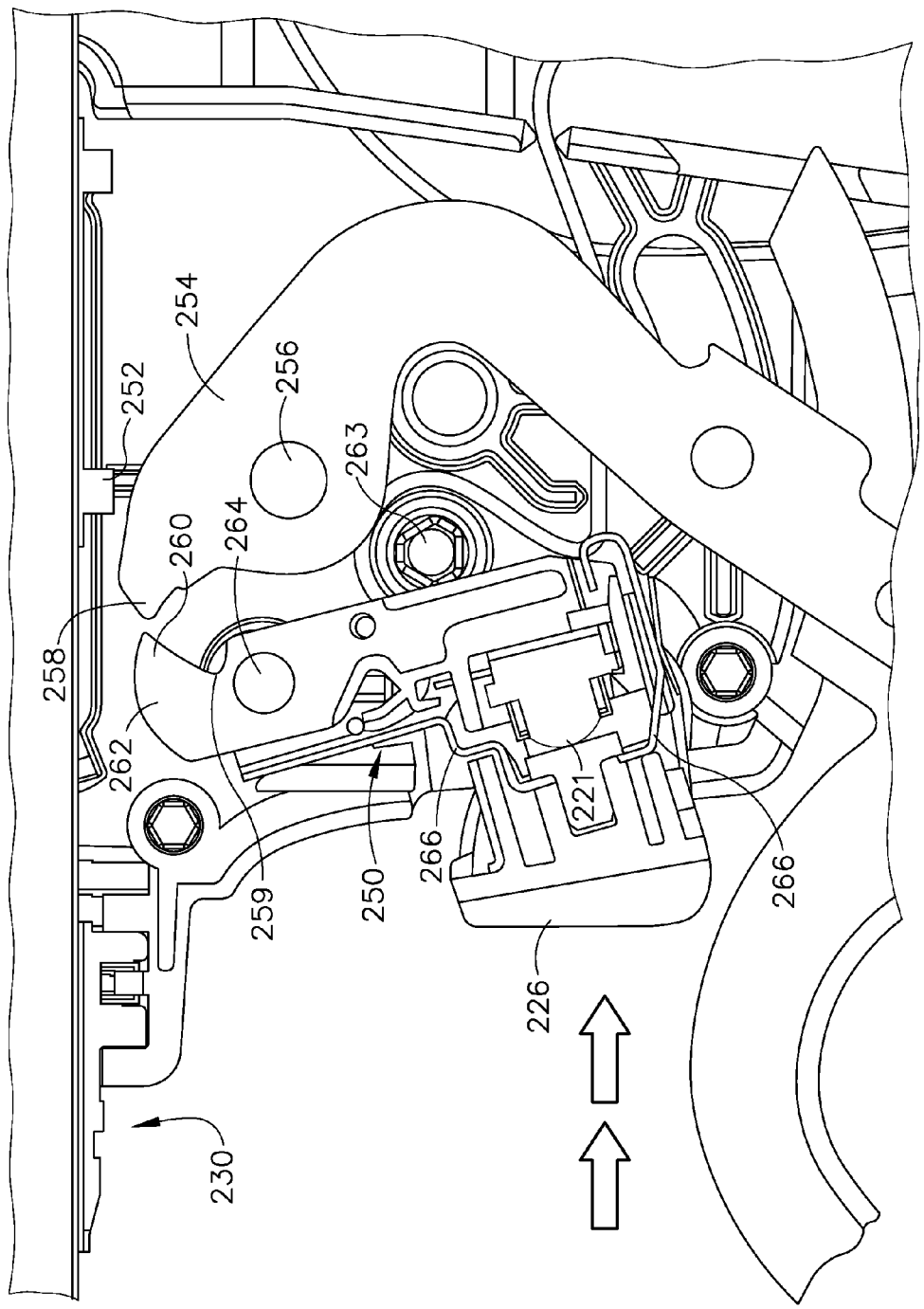
FIG. 11C depicts an enlarged side view of the lockout mechanism of FIG. 10 in a third position with the button fully depressed and the lockout mechanism released.
Figure 11D:
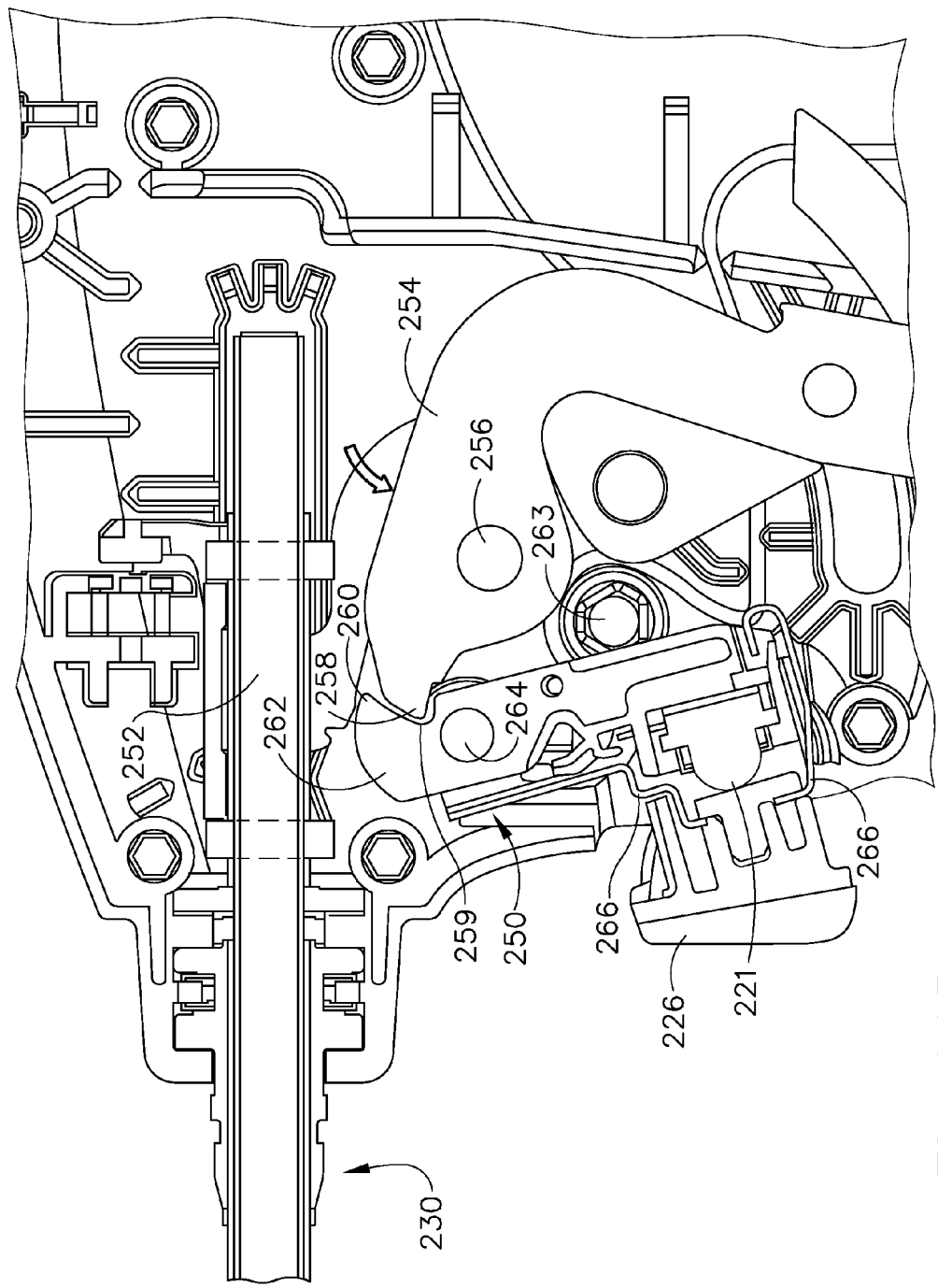
FIG. 11D depicts an enlarged side view of the lockout mechanism of FIG. 10 in a fourth position with the firing beam advanced.

FIG. 11C shows activation button (226) fully depressed. Activation button (226) has been sufficiently pushed at this stage such that lockout lever (262) pivots about trigger pin (264). A boss (263) in handpiece (220) arrests pivoting of lockout lever (262) at this stage. As seen in FIG. 11C, hook stopper (260) rotates counter clockwise in response to activation button (226) being fully depressed. Furthermore, hook stopper (260) moves from under distal projection (258) such that it no longer blocks distal projection (258). In the exemplary version, hook stopper (260) moves such that it provides just enough clearance for distal projection (258), but it will be appreciated that hook stopper (260) may be configured to move any suitable distance to provide clearance for distal projection (258). Since hook stopper (260) has provided clearance for distal projection (258), the operator may then pull pivoting trigger (224). FIG. 11D shows lockout mechanism (250) after pivoting trigger (224) has been pulled. Lockout arm (254) pivots about arm pin (256). As a result, distal projection (258) rotates and moves into a notch (259) of lockout lever (262). Furthermore, angled link (223) longitudinally advances firing beam driver (252). This drives firing tube (249) distally, thereby driving the firing beam and distal blade distally through the end effector to sever tissue.

In view of the foregoing, it should be understood that button (226) may be pressed through a first range of motion (FIGS. 11A-11B) to activate RF energy; then through a second range of motion (FIGS. 11B-11C) to unlock full distal advancement of a firing beam by enabling full pivoting of trigger (224). Friction between distal projection (258) and lockout lever (262) may provide the operator with tactile feedback indicating completion of the first range of motion. In other words, the user may feel sudden increased resistance in button (226) after completing the first range of motion. Other features (e.g., detent features, etc.) may be provided to enhance this tactile feedback and/or to provide some other kind of feedback (e.g., audio, visual, etc.). It should also be understood that button (126) of handpiece (120) may also be operable to move through first and second ranges of motion just like button (226) described above. In particular, button (126) may remove through a first range of motion to activate RF energy at the end effector at the distal end of shaft (130); then through a second range of motion to unlock lockout mechanism (150).

It will be appreciated that angled link (223) and pivoting trigger (224) may be spring biased to reverse the direction of their pivot to return to the position shown in FIG. 11A after trigger (224) is released. Similarly, lockout lever (262) also may be spring biased to return to the position shown in FIG. 11A as well. It should also be understood that pivoting trigger (224) may be configured to pivot through a first range of motion before reaching the locked out position shown in FIG. 11A. Such a first range of motion may provide closure of the jaws of the end effector as described above. Thus, an operator may clamp on tissue before activating the electrodes with RF energy, then seal the tissue with the RF energy for as long as desired before pressing further on button (226) to unlock the firing beam for further, tissue severing advancement.

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012 (now U.S. Pat. No. 9,161,803, issued Oct. 20, 2015), the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603 (expired), filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193 (now U.S. Pat. No. 8,408,439), entitled "Surgical Stapling Instrument with An Articulatable End Effector," published Oct. 21, 2010; and U.S. Pub. No. 2012/0239012 (now U.S. Pat. No, 8,453,914), entitled "Motor-Driven Surgical Cutting Instrument with Electric Actuator Directional Control Assembly," published Sep. 20, 2012. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874 (abandoned), entitled "Tissue Pad for Use with an Ultrasonic Surgical Instrument," published Apr. 13, 2006, the disclosure of which is incorporated by reference herein; U.S. Pat. Pub. No. 2007/0191713 (abandoned), entitled "Ultrasonic Device for Cutting and Coagulating," published Aug. 16, 2007, the disclosure of which is incorporated by reference herein; U.S. Pat. Pub. No. 2007/0282333 (abandoned), entitled "Ultrasonic Waveguide and Blade," published Dec. 6, 2007, the disclosure of which is incorporated by reference herein; U.S. Pat. Pub. No. 2008/0200940 (abandoned), entitled "Ultrasonic Device for Cutting and Coagulating," published Aug. 21, 2008, the disclosure of which is incorporated by reference herein; U.S. Pat. Pub. No. 2011/0015660 (now U.S. Pat. No. 8,461,744), entitled "Rotating Transducer Mount for Ultrasonic Surgical Instruments," published Jan. 20, 2011, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011 (now U.S. Pat. No. 8,939,974, issued Jan. 27, 2015), the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) an end effector operable to manipulate tissue;
   (b) a shaft in communication with the end effector, wherein the shaft comprises:
      (i) a firing beam operable to actuate a portion of the end effector, and
      (ii) a firing beam driver operable to drive the firing beam; and
   (c) a handpiece in communication with the end effector, wherein the handpiece comprises:
      (i) a pivoting trigger, wherein the pivoting trigger is configured to distally advance the firing beam driver to advance the firing beam,
      (ii) an activation button, and
      (iii) a lockout assembly operable to transition between a locked state and an unlocked state, wherein the lockout assembly in the locked state is configured to block a portion of the firing beam driver from advancing, wherein the lockout assembly in the unlocked state is configured to allow the firing beam driver to advance, wherein the activation button is in communication with the lockout assembly, wherein the activation button is configured to switch the lockout assembly from the locked state to the unlocked state,
      wherein the lockout assembly comprises a first pivoting member configured to selectively engage the firing beam driver to thereby selectively restrict motion of the firing beam driver, wherein the first pivoting member is pivotably secured to the handpiece.

2. The apparatus of claim 1, wherein the firing beam driver comprises a spool.

3. The apparatus of claim 2, wherein the spool has an annular flange, wherein the first pivoting member is operable to selectively engage the flange.

4. The apparatus of claim 3, wherein the first pivoting member has a proximally presented shoulder, wherein the proximally presented shoulder is configured to arrest distal motion of the flange.

5. The apparatus of claim 2, wherein the first pivoting member is configured to pivot away from the annular flange in response to movement of the activation button.

6. The apparatus of claim 1, wherein the activation button is moveable between a home position, a first position, and a second position, wherein the activation button in the first position is configured to activate energy delivery at the end effector, wherein the activation button in the second position is configured to switch the lockout assembly to the unlocked state.

7. The apparatus of claim 6, wherein the activation button is in communication with one or more tangs configured to bias the activation button.

8. The apparatus of claim 1, further comprising a lockout spring in communication with the first pivoting member, wherein the lockout spring is configured to bias the first pivoting member into engagement with the firing beam driver.

9. The apparatus of claim 1, wherein the first pivoting member comprises a lockout arm, wherein the lockout assembly further comprises:
   (i) a lockout lever, and
   (ii) a linking arm, wherein the lockout arm is coupled with the linking arm, wherein the linking arm is in communication with the lockout lever.

10. The apparatus of claim 9, wherein the linking arm comprises a slot, wherein the lockout arm comprises a slot pin, wherein the slot pin is slidably disposed in the slot.

11. The apparatus of claim 9, wherein the lockout lever is in communication with the activation button, wherein the lockout lever is configured to pivot the linking arm about a pin in response to movement of the activation button.

12. The apparatus of claim 1, wherein the end effector comprises a clamping jaw, wherein the firing beam is operable to pivot the clamping jaw in response to advancement of the firing beam through a first range of motion.

13. The apparatus of claim 12, wherein the lockout assembly is configured to enable advancement of the firing beam through the first range of motion before engagement between the first pivoting member and the firing beam driver.

14. The apparatus of claim 13, wherein the firing beam is operable to sever tissue clamped by the clamping jaw in response to advancement of the firing beam through a second range of motion.

15. The apparatus of claim 14, wherein the first pivoting member is configured to arrest the firing beam driver upon completion of the first range of motion by the firing beam, and before initiation of the second range of motion by the firing beam.

16. The apparatus of claim 1, wherein the end effector is operable to deliver RF energy to tissue.

17. An apparatus for operating on tissue, the apparatus comprising:
   (a) an end effector operable to manipulate tissue;
   (b) a shaft in communication with the end effector, wherein the shaft comprises a firing beam operable to actuate a portion of the end effector; and
   (c) a handpiece in communication with the end effector, wherein the handpiece comprises:
      (i) a pivoting trigger, wherein the pivoting trigger is configured to distally advance the firing beam, wherein the pivoting trigger comprises a first pivoting arm, and (ii) a lockout assembly movable between a locked state and an unlocked state, wherein the lockout assembly comprises a second pivoting arm, wherein the second pivoting arm is configured to directly engage the first pivoting arm and thereby block pivoting of the first pivoting arm when the lockout assembly is in the locked state, wherein the second pivoting arm is configured to disengage the first pivoting arm and thereby enable pivoting of the first pivoting arm when the lockout assembly is in the unlocked state.

18. The apparatus of claim 17, wherein the second pivoting arm comprises a hook stopper, wherein the first pivoting arm comprises a distal projection, wherein the hook stopper is configured to selectively block movement of the distal projection.

19. The apparatus of claim 18, wherein the distal projection is positionable to rest on the hook stopper, wherein the hook stopper is spring biased to remain under the distal projection.

20. An apparatus for operating on tissue, the apparatus comprising:
   (a) an end effector operable to compress tissue, wherein the end effector is further operable to deliver RF energy to tissue;
   (b) a shaft in communication with the end effector, wherein the shaft comprises a firing beam, wherein the firing beam is movable through a first range of motion to compress tissue, wherein the firing beam movable through a second range of motion to sever tissue compressed by the end effector; and
   (c) a handpiece in communication with the end effector, wherein the handpiece comprises:
      (i) a pivoting trigger, wherein the pivoting trigger is operable to drive the firing beam,
      (ii) an activation button operable to selectively activate RF energy at the end effector, and
      (iii) a lockout assembly operable to transition between a first state and a second state,
   wherein the lockout assembly comprises a first pivoting member configured for direct engagement with either the shaft or the pivoting trigger,
   wherein the first pivoting member is pivotably secured to the handpiece,
   wherein the lockout assembly is configured to permit the firing beam to move through the first range of motion yet prevent the firing beam from moving through the first range of motion when the lockout assembly is in the first state,
   wherein the lockout assembly is configured to permit the firing beam to move through the second range of motion when the lockout assembly is in the second state,
   wherein the activation button is operable to switch the lockout assembly from the first state to the second state.

* * * * *